United States Patent
Okamura et al.

(10) Patent No.: US 11,918,805 B2
(45) Date of Patent: Mar. 5, 2024

(54) SKIN STIMULATION BRUSH

(71) Applicant: G.M CORPORATION CO., LTD., Osaka (JP)

(72) Inventors: Yuko Okamura, Osaka (JP); Takashi Hosokawa, Osaka (JP); Manami Matsuoka, Osaka (JP); Fujio Aramoto, Osaka (JP)

(73) Assignee: G.M Corporation, Osaka (JP)

( * ) Notice: Subject to any disclaimer, the term of this patent is extended or adjusted under 35 U.S.C. 154(b) by 0 days.

(21) Appl. No.: 18/019,472

(22) PCT Filed: Aug. 6, 2021

(86) PCT No.: PCT/JP2021/029385
§ 371 (c)(1),
(2) Date: Mar. 21, 2023

(87) PCT Pub. No.: WO2022/030630
PCT Pub. Date: Feb. 10, 2022

(65) Prior Publication Data
US 2023/0256241 A1 Aug. 17, 2023

(30) Foreign Application Priority Data
Aug. 6, 2020 (JP) .................................. 2020-134121

(51) Int. Cl.
*A61N 1/32* (2006.01)
*A46B 15/00* (2006.01)
(Continued)

(52) U.S. Cl.
CPC .......... *A61N 1/322* (2013.01); *A46B 15/0022* (2013.01); *A46D 1/0207* (2013.01);
(Continued)

(58) Field of Classification Search
CPC ...... A61N 1/322; A61N 1/0476; A61N 1/328; A61N 1/36014; A46B 15/0022; A46B 2200/102; A46D 1/0207
See application file for complete search history.

(56) References Cited

U.S. PATENT DOCUMENTS

| 8,131,381 B1 | 3/2012 | Santjer |
| 2004/0077977 A1* | 4/2004 | Ella .................... A61H 23/0245 601/9 |

(Continued)

FOREIGN PATENT DOCUMENTS

| CN | 1893903 A | 1/2007 |
| CN | 107583193 A | 1/2018 |

(Continued)

OTHER PUBLICATIONS

Mill-Max Mfg. Corp., Spring-Loaded Pins Data Sheet for Product No. 0914, pre—Mar. 3, 2011, https://www.mouser.com/datasheet/2/273/025-259718.pdf.*

(Continued)

*Primary Examiner* — Timothy A Stanis
(74) *Attorney, Agent, or Firm* — Modal PLLC

(57) ABSTRACT

A skin stimulation brush includes stimulation brush pins, each including a base bottom member made of a metal, which is connected to an electric circuit so as to allow conduction of electricity from the electric circuit; a body member being an elongated tubular body, which has a proximal end portion at which the base bottom member is disposed; an electrode member connected to an opening of the body member on a distal end side, and having a distal end being exposed; and a metal shaft inserted into a tubular inner portion of the body member with an air gap, which is configured to couple the base bottom member and the electrode member while being in a compressed state in a length direction of the body member. The metal shaft has (Continued)

pliability that allows bending in a radial direction. The body member has elasticity that allows bending in a radial direction.

12 Claims, 4 Drawing Sheets

(51) Int. Cl.
  *A46D 1/00* (2006.01)
  *A61N 1/04* (2006.01)
  *A61N 1/36* (2006.01)

(52) U.S. Cl.
  CPC ........... *A61N 1/0476* (2013.01); *A61N 1/328* (2013.01); *A61N 1/36014* (2013.01); *A46B 2200/102* (2013.01)

(56) References Cited

U.S. PATENT DOCUMENTS

| | | | |
|---|---|---|---|
| 2011/0054288 A1* | 3/2011 | Besio | A61B 5/291 600/383 |
| 2014/0222026 A1* | 8/2014 | Tenenbaum | A61N 7/00 606/131 |
| 2014/0330196 A1 | 11/2014 | Ingman et al. | |
| 2015/0053227 A1* | 2/2015 | Sugunan | A45D 7/00 132/142 |
| 2015/0265825 A1* | 9/2015 | Miller | A61M 37/0092 604/20 |
| 2020/0253811 A1* | 8/2020 | Alexander | A61L 31/14 |

FOREIGN PATENT DOCUMENTS

| | | |
|---|---|---|
| CN | 208837183 U | 5/2019 |
| CN | 110731597 A | 1/2020 |
| JP | S64-020859 U | 2/1989 |
| JP | S64-034047 U | 3/1989 |
| JP | H3-16949 U | 2/1991 |
| JP | 3005990 U | 10/1994 |
| JP | 2000-140131 A | 5/2000 |
| JP | 2003-319835 A | 11/2003 |
| JP | 2004-121327 A | 4/2004 |
| JP | 3127930 U | 11/2006 |
| JP | 2009-247526 A | 10/2009 |
| JP | 2013183890 A | 9/2013 |
| JP | 2014-527432 A | 10/2014 |
| KR | 20190077278 A | 7/2019 |
| WO | 2013021380 A1 | 2/2013 |

OTHER PUBLICATIONS

Mill-Max, Data Sheet for Product No. 0914-0-15-20-77-14-11-0; https://www.mouser.com/datasheet/2/273/MMMC_S_A0006083727_1-2558442.pdf; website visited Sep. 27, 2023 (Year: 2018).*
First Office Action in corresponding Chinese App. No. 202180005415.6, dated Feb. 23, 2023, 10 pages, CNIPA.
International Search Report in Int'l App. No. PCT/JP2021/029385, dated Feb. 7, 2021, 3 pages, Japan Patent Office.
International Preliminary Report on Patentability in Int'l App. No. PCT/JP2021/029385, dated Feb. 7, 2023, 8 pages, WIPO.
Written Opinion of the International Searching Authority in Int'l App. No. PCT/JP2021/029385, dated Sep. 7, 2021, 6 pages, Japan Patent Office.
Notice of Reasons for Refusal in corresponding Japanese App. No. 2020134121, dated May 6, 2021, 10 pages, Japan Patent Office.
First Office Action in corresponding Chinese App. No. 202180005415.6, dated Feb. 23, 2023, 11 pages, CNIPA.
Ya-Man Ltd., Written Request for Trial, Invalidity Trial No. 2022-800040, May 2, 2022, 338 pages, Japan Patent Office.
G.M Corporation, Written Answer, Invalidity Trial No. 2022-800040, Aug. 29, 2022, 119 pages, Japan Patent Office.
Written Statement of Oral Proceedings, Invalidity Trial No. 2022-800040, dated Jan. 18, 2023, 380 pages, Japan Patent Office.
Ya-Man Ltd., Petition, Invalidity Trial No. 2022-800040, Feb. 24, 2023, 80 pages, Japan Patent Office.
Sasaki Hiroshi, Trial Decision, Invalidity Trial No. 2022-800040, Jun. 28, 2023, 94 pages, Japan Patent Office.

* cited by examiner

SKIN STIMULATION BRUSH

TECHNICAL FIELD

The present invention relates to a skin stimulation brush that electrically stimulates skin.

BACKGROUND ART

There is known a related-art brush that is made of, for example, a resin. The related-art brush includes a handle, a brush base, and a plurality of bristles. The brush base is provided at a distal end of the handle. The plurality of bristles are provided upright on the brush base.

Further, there is known a hair growth brush having the following configuration as a brush with which a scalp can be massaged. Specifically, the hair growth brush includes a container that stores a solution such as a hair growth product, bristles that are connected to the container to discharge the solution onto a scalp, a power source for a current that electrically stimulates a living body, and bristles that are connected to the power source to allow the current to flow to the scalp.

BRIEF SUMMARY

In the related art, however, the bristles that allow a current to flow to skin are exposed on a surface. Thus, there is a problem in that the bristles may swell and degrade due to a drug such as a hairdressing product or sweat and thus electroconductivity is lowered with use.

In order to solve the above-mentioned problem, according to the present invention, there is provided a skin stimulation brush, including: a housing that forms a handle and a brush base provided to one end of the handle; an electric circuit accommodated in the housing; and a plurality of skin stimulation brush pins provided to the brush base in a protruding manner, wherein each of the skin stimulation brush pins includes: a base bottom member made of a metal, which is connected to the electric circuit so as to allow conduction of electricity from the electric circuit; a body member being an elongated tubular body, which has a proximal end portion at which the base bottom member is disposed; an electrode member, which is connected to an opening of the body member on a distal end side, and has a distal end being exposed; and a metal shaft inserted into a tubular inner portion of the body member with an air gap, which is configured to couple the base bottom member and the electrode member.

According to the above-mentioned configuration, the metal shaft that applies a current to the electrode member is inserted into the tubular inner portion of the body member. Thus, the metal shaft is not brought into direct contact with sebum, water, shampoo, a cosmetic product, or the like, which adheres to skin or body hair. As a result, corrosion of the metal shaft serving as a path for a current from the electric circuit to the electrode member can be suppressed, and lowering of electroconductivity can be suppressed for a long period of time.

Further, the electrode member may have corrosion resistance.

In this case, the electrode member, which is brought into direct contact with skin, has corrosion resistance. Thus, even when sebum, water, shampoo, a cosmetic product, or the like adheres to the electrode member, the electrode member is less liable to rust. As a result, corrosion of the electrode member is suppressed, and lowering of electroconductivity of the electrode member can be suppressed.

Further, the electrode member may be made of stainless steel. Further, copper, aluminum, silver, gold, or gold may be used.

Further, the metal shaft may have pliability that allows bending in a radial direction, and the body member may have elasticity that allows bending in a radial direction.

A "radial direction" refers to a radial direction when it is assumed that a length direction of the skin stimulation brush pin is an axial direction. However, this description does not limit a shape of the metal shaft or the body member to a columnar shape or a cylindrical shape.

In this case, the body member and the metal shaft inserted into the tubular inner portion of the body member can be bent in the radial direction. Thus, the skin stimulation brush pins can be bent in the radial direction in accordance with a force applied from skin to the skin stimulation brush pins during the use of the skin stimulation brush pins. Thus, the skin stimulation brush pins can achieve a massaging effect produced by elasticity from a bent state achieved along with pressure on skin. Further, in combination with the above-mentioned configuration, reliable electroconductivity can be provided by the metal shaft. In addition, an effect of suppressing lowering of electroconductivity with elapse of time, which is caused by the contact with, for example, sebum, water, shampoo, or a cosmetic product, can be produced.

Further, it is preferred that the metal shaft be formed of a spring. An axially elongated spring is preferred as the spring. More specifically, suitable examples of the spring include a leaf spring and a coil spring. The metal shaft is a coil spring that urges the electrode member toward a distal end side. When a force acting toward a proximal end side is applied to the electrode member, the electrode member may be thrust toward the proximal end side against an urging force of the coil spring.

In this case, the electrode member can be thrust toward the proximal end side against the urging force of the coil spring. Thus, when the skin stimulation brush pin is brought into contact with skin, the electrode member is thrust toward the proximal end side by a pressure generated as a result of the contact with the skin. Further, the urging force of the coil spring is applied to the electrode member toward the distal end side under a state in which the electrode member is thrust toward the proximal end side. As a result, when the electrode member presses skin, an impact generated by the contact between the electrode member and the skin is alleviated. In this manner, the degree of force applied by a user can easily be adjusted.

Further, the body member may have flexibility in the length direction, and when the electrode member is thrust toward a proximal end side, the body member may be compressed in the length direction.

In this case, when the electrode member is thrust toward the proximal end side, the body member is compressed in the length direction. Further, the body member has flexibility. Thus, when the electrode member is thrust toward the proximal end side, not only the urging force of the coil spring but also a restoring force of the body member is applied to the distal end side. As a result, even when the electrode member strongly presses skin, the skin of the user of the skin stimulation brush pins is not unexpectedly damaged. Further, the urging force and the restoring force can provide pressure feeling with comfortable stimulation to the user while ensuring reliable contact between the electrode member and the skin.

Further, the body member may have water resistance.

In this case, when the body member has water resistance, intrusion of water into the tubular inner portion of the body member can be suppressed. Thus, the contact of water with the metal shaft that is inserted into the tubular inner portion can be suppressed. As a result, corrosion of the metal shaft can be suppressed, and thus lowering of electroconductivity of the metal shaft can be suppressed.

Further, the body member may be made of a silicone rubber.

In this case, the silicone rubber has water resistance and is safe to a human body. Thus, the skin stimulation brush pins can be used without anxiety.

Further, the electric circuit may be configured to be capable of applying a low-frequency current to the electrode member from the base bottom member via the metal shaft.

In this case, the low-frequency current applied to the base bottom member flows through the metal shaft to cause conduction of electricity through the electrode member. Thus, when the electrode member conducting electricity is brought into contact with skin, the low-frequency current is applied to the skin. Further, the low-frequency current has a property of acting on the vicinity of a skin surface. As a result, electric stimulation can be applied particularly to the vicinity of a skin surface as a target.

According to the present invention, the metal shaft is not brought into direct contact with sebum, water, shampoo, a cosmetic product, or the like, which adheres to skin or body hair. Thus, the corrosion of the metal shaft can be suppressed. Accordingly, lowering of electroconductivity of the metal shaft can be suppressed. As a result, a skin stimulation brush with suppression of lowering of electroconductivity can be provided. User's need to maintain intensity of the electric stimulation can also be satisfied.

Further, when the body member is configured to have the tubular body with elasticity in the radial direction and flexibility in the length direction, strong pressure applied by the electrode member onto the skin of the user of the skin stimulation brush does not unexpectedly damage the skin. Further, the urging force and the restoring force can provide pressure feeling with comfortable stimulation to the user while ensuring reliable contact between the electrode member and the skin.

Further, according to the present invention, the low-frequency current applied from the electrode member to skin can increase blood flow in the skin to activate the metabolism of cells. As a result, when the skin of an area having hair is stimulated, hair loss can be suppressed. Further, when a facial skin is stimulated, a rapid skin lift-up effect can be exerted. Thus, a skin condition before makeup is improved, and makeup sits better.

Further, the skin lift-up effect can also contribute to a firming effect on a skin other than a facial skin, and can suppress sagging of the skin.

DETAILED DESCRIPTION

Now, an embodiment of the present invention is described in detail with reference to the accompanying drawings. Components having substantially the same functions and configurations are denoted by the same reference symbols in this specification and the drawings, and an overlapping description thereof is herein omitted. Moreover, the embodiment given below shows an example of the present invention. Therefore, the technical scope of the present invention is not limited to this embodiment.

Figure 1:
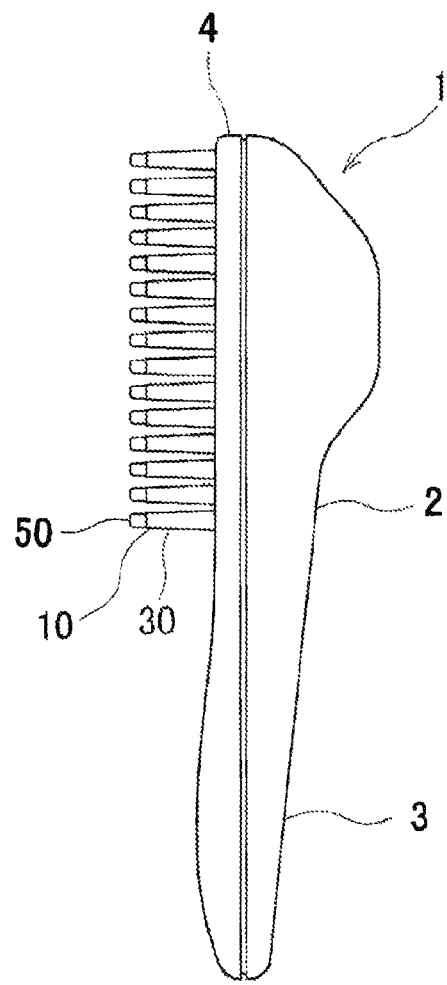
FIG. 1 is a left side view of a skin stimulation brush (1).
Figure 2:
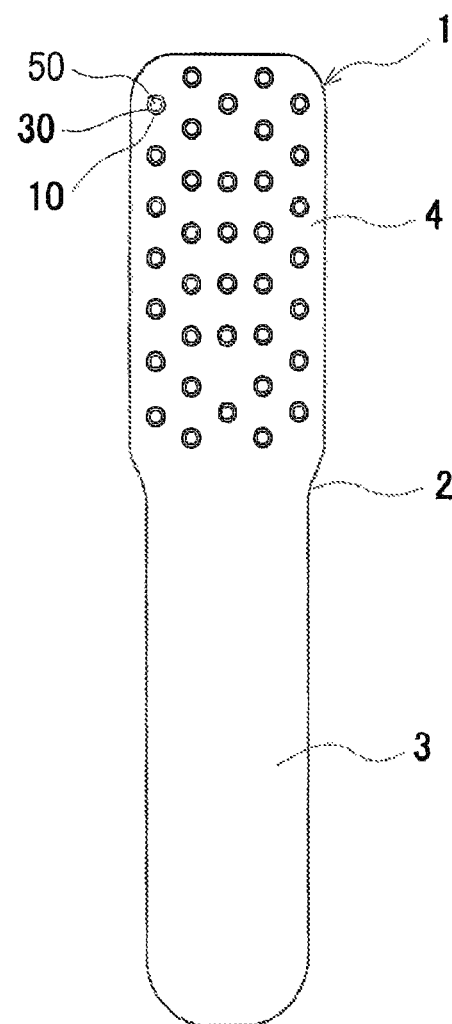
FIG. 2 is a front view of the skin stimulation brush (1).

First, with reference to FIG. 1 and FIG. 2, an example of a configuration of a skin stimulation brush 1 according to this embodiment is described. FIG. 1 is a left side view of the skin stimulation brush 1. FIG. 2 is a front view of the skin stimulation brush 1.

The skin stimulation brush 1 includes a handle 3 and a brush base 4 provided to one end of the handle 3. The handle 3 and the brush base 4 are formed of a housing 2. A plurality of skin stimulation brush pins 10 are provided to the brush base 4 in a protruding manner. An electric circuit 6 is accommodated in the housing 2.

The handle 3 has an elliptic cylindrical shape with a diameter that increases from a lower end toward an intermediate portion and then decreases toward an upper end. One end of the handle 3 is connected to the brush base 4. The handle 3 is a portion to be gripped by a user. The handle 3 is made of, for example, a resin. A peripheral surface of the handle 3 is formed as the housing 2.

The brush base 4 is formed in a block-like shape with a protruding back surface. One end of the brush base 4 is connected to one end of the handle 3. The plurality of skin stimulation brush pins 10 are provided to the brush base 4 in a protruding manner. The brush base 4 may be made of, for example, a resin. A peripheral surface of the brush base 4 is formed as the housing 2. A plurality of brush-base holes 5 into which the skin stimulation brush pins 10 are inserted may be formed in the brush base 4. The brush-base holes 5 are formed as small holes passing through the housing 2. The brush-base holes 5 are formed in one side surface of the brush base 4 in a dispersed manner. In one example described in this embodiment, the brush base 4 is formed in a block-like shape with a protruding back surface, and has the brush-base holes 5 formed therein. However, a shape of the brush base 4 is not limited to thereto. The brush base 4 may have any shape as long as the plurality of skin stimulation brush pins 10 can be provided thereto in a protruding manner. For example, body portions 30 of the skin stimulation brush pins 10 and the brush base 4 may be formed integrally instead of forming the brush-base holes 5.

The handle 3 and the brush base 4 are formed by joining two housings 2 divided into a front part and a rear part. The handle 3 and the brush base 4 may be formed integrally, or the handle 3 and the brush base 4, which are independent of each other, may be joined together at one end of the handle 3 and one end of the brush base 4.

The housing 2 forms the handle 3 and the brush base 4. The electric circuit 6 is accommodated inside the housing 2. The housing 2 may accommodate not only the electric circuit 6 but also a battery or a cell, which is connected to the electric circuit 6. A connector to be used for charging may be provided to the housing 2. The housing 2 may accommodate a cell case.

The electric circuit 6 is accommodated in the housing 2. The electric circuit 6 may be formed of a printed circuit board. The electric circuit 6 has a plurality of through holes 7 formed therein. The through holes 7 are formed at positions corresponding to the brush-base holes 5 when the electric circuit 6 is accommodated in the housing 2. A battery or a cell may be connected to the electric circuit 6. The electric circuit 6 may be configured to be capable of applying a low-frequency current to base bottom members 20. For example, publicly known various low-frequency current generators or low-frequency modulators may be provided to the electric circuit 6.

Figure 3:
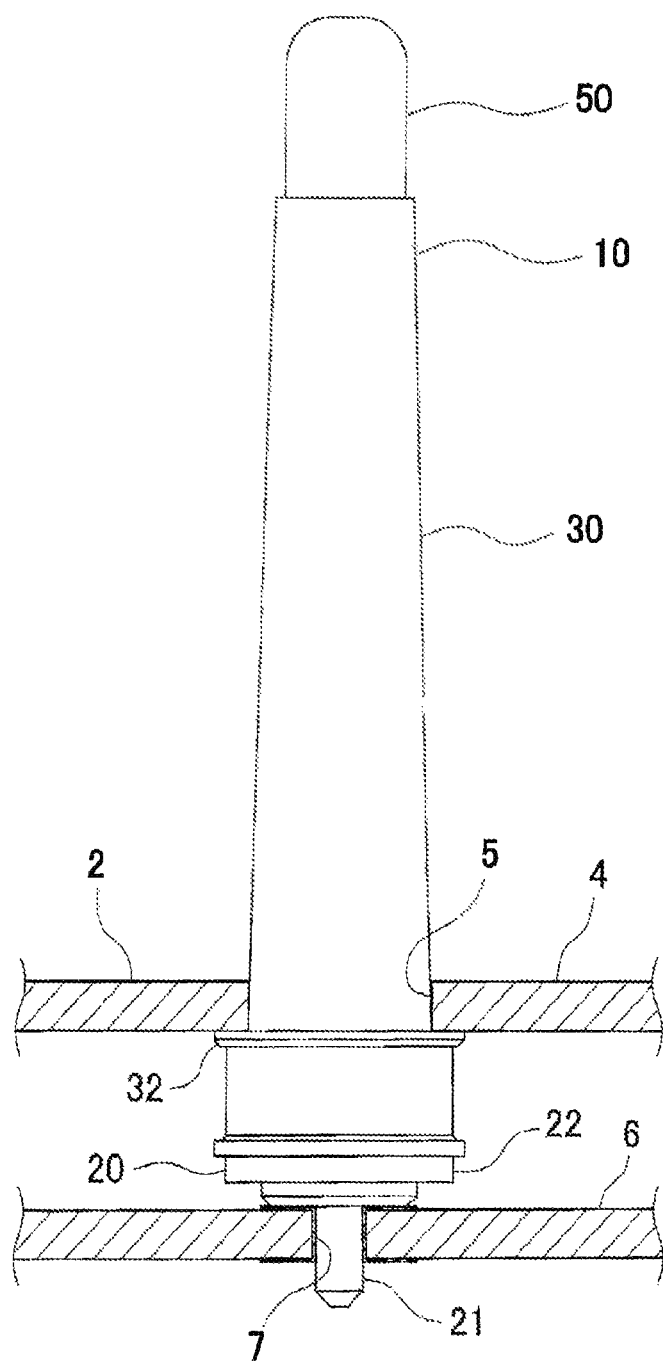
FIG. 3 is an enlarged view of a skin stimulation brush pin (10) of the skin stimulation brush (1) according to the present invention.
Figure 4:
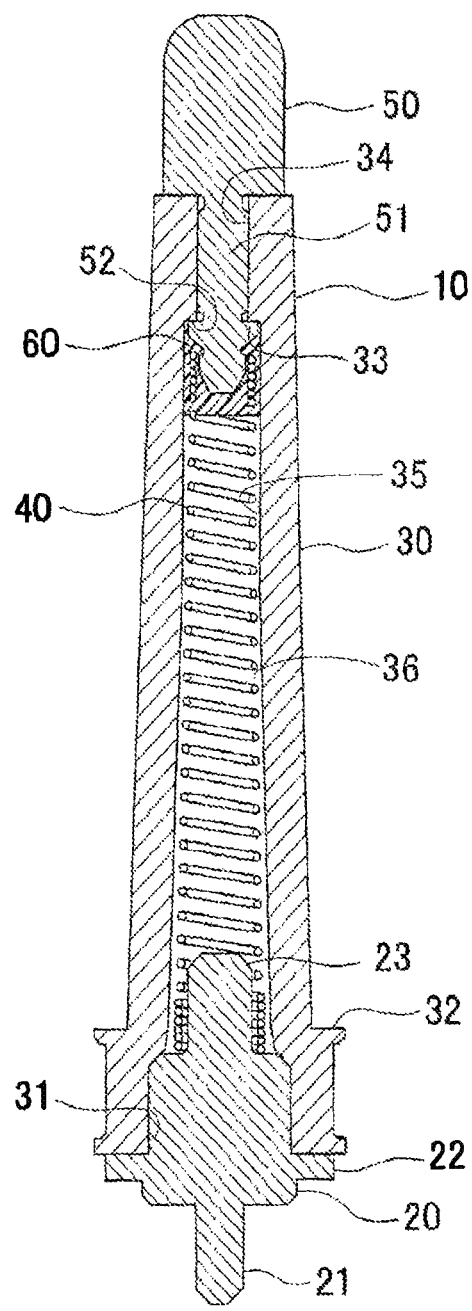
FIG. 4 is an enlarged sectional view of the skin stimulation brush pin (10) of the skin stimulation brush (1) according to the present invention.

Next, with reference to FIG. 3 and FIG. 4, an example of the skin stimulation brush pin 10 of the skin stimulation brush 1 according to this embodiment is described. FIG. 3 is an enlarged view of the skin stimulation brush pin 10 of the skin stimulation brush 1 according to the present invention. FIG. 4 is an enlarged sectional view of the skin stimulation brush pin 10 of the skin stimulation brush 1 according to the present invention.

The skin stimulation brush pin 10 includes the base bottom member 20 made of a metal, which can be connected to the electric circuit 6 so as to allow conduction of electricity from the electric circuit 6. The skin stimulation brush pin 10 includes the body member 30, which is an elongated tubular body. The base bottom member 20 is disposed at a proximal end portion of the body member 30. The skin stimulation brush pin 10 includes an electrode member 50. The electrode member 50 is connected to a distal-end opening portion 34 being an opening formed on a distal end side of the body member 30, and has a distal end being exposed. The skin stimulation brush pin 10 includes a metal shaft 40. The metal shaft 40 is inserted into the tubular inner portion of the body member 30 to thereby couple the base bottom member 20 and the electrode member 50 to each other.

The base bottom member 20 is formed as a rotary body having an axis extending in a length direction of the skin stimulation brush pin 10 as a center. The base bottom member 20 is formed to be solid. A pin 21 having an elongated shape is formed in a protruding manner at a proximal end portion of the base bottom member 20. The pin 21 is provided so as to protrude from a main body of the base bottom member 20 toward a proximal end side. A base bottom flange 22 is formed on a side periphery of the main body portion of the base bottom member 20. A base bottom protruding portion 23 having a columnar shape is formed in a protruding manner at a distal end portion of the base bottom member 20. The base bottom member 20 is made of a metal. The base bottom member 20 is made of stainless steel.

As illustrated in FIG. 3, the base bottom member 20 is connected to the electric circuit 6 so as to allow conduction of electricity from the electric circuit 6. The pin 21 of the base bottom member 20 is inserted into the through hole 7. When the pin 21 is inserted into the through hole 7, the pin 21 and the through hole 7 are brought into contact with each other to thereby connect the base bottom member 20 to the electric circuit 6. In one example described in this embodiment, the base bottom member 20 is connected to the electric circuit 6 through the contact of the pin 21 with the through hole 7. However, a connection method to the electric circuit 6 is not limited thereto. Various methods can be used as long as the base bottom member 20 is connected to the electric circuit 6. For example, an electroconductive cord connected to the electric circuit 6 may be connected to the base bottom member 20.

As illustrated in FIG. 3 and FIG. 4, in one example described in this embodiment, the base bottom member 20 is formed as an independent component. However, a configuration of the base bottom member 20 is not limited thereto. Various methods can be used as long as conduction of electricity through the metal shaft 40 is allowed. For example, the base bottom member 20 may be formed integrally with a proximal end portion of the metal shaft 40 as a part of the metal shaft 40.

The body member 30 is an elongated tubular body, and has a proximal end portion at which the base bottom member 20 is disposed. The body member 30 is formed in a cylindrical shape. The body member 30 is formed with a diameter decreasing toward its distal end. The body member 30 has an outer diameter gradually decreasing toward the distal end and an inner diameter correspondingly gradually decreasing toward the distal end. The body member 30 has a proximal-end opening portion 31 and the distal-end opening portion 34. The proximal-end opening portion 31 is an opening on the proximal end side, and the distal-end opening portion 34 is an opening on the distal end side. The body member 30 has a body stopper portion 32 having a flange-like shape. The body stopper portion 32 is formed on an outer peripheral surface of the proximal end portion of the body member 30. The body member 30 has a radially contracted portion 33 at which an inner diameter is reduced. The radially contracted portion 33 forms a level difference on an inner surface of the distal end portion. An upper half part of the base bottom member 20 is inserted and fitted into the proximal-end-side opening portion of the body member 30 toward the distal end side.

An edge of the proximal-end opening portion 31 at the proximal end of the body member 30 is in contact with a surface of the base bottom flange 22 of the base bottom member 20 on the distal end side. The body stopper portion 32 of the body member 30 is in contact with an inner surface of the housing 2. The body stopper portion 32 of the body member 30 is caught by an edge of the brush-base hole 5 of the housing 2 so as not to be removed from the brush-base hole 5. The edge of the proximal-end opening portion 31 at the proximal end of the body member 30 is in contact with the surface of the base bottom flange 22 of the base bottom member 20 on the distal end side, while a surface of the body stopper portion 32 on the distal end side is in contact with the inner surface of the housing 2. Thus, the proximal end portion of the body member 30 is fixed to the brush base 4.

It is preferred that the body member 30 have elasticity that allows bending in a radial direction with respect to an axis extending in the length direction of the skin stimulation brush pin 10. Further, it is more preferred that the body member 30 be made of a silicone rubber.

The body member 30 may have flexibility in the length direction. Further, it is preferred that the body member 30 have flexibility in the length direction and be formed so as to be compressible in the length direction when the electrode member 50 is thrust toward the proximal end side.

It is preferred that the body member 30 have water resistance.

In one example described in this embodiment, the body member 30 is formed in a cylindrical shape. However, the shape of the body member 30 is not limited thereto. The body member 30 may be formed as an elongated tubular body having various shapes. A sectional shape of the body member 30 may be, for example, circular, elliptical, rectangular, or pentagonal.

The proximal end portion of the body member 30 is disposed without leaving a gap from the brush base 4. Thus, the stopper portion 32 of the body member 30 is in contact with the inner surface of the housing 2 to thereby achieve sealing.

The base bottom member 20 is disposed at the proximal end portion of the body member 30 without leaving a gap. The base bottom member 20 is fitted into the proximal-end opening portion 31 of the body member 30 so as to be in close contact therewith.

The metal shaft 40 is inserted into the tubular inner portion of the body member 30 to thereby couple the base bottom member 20 and the electrode member 50 to each other. A proximal end of the metal shaft 40 is in contact with the base bottom member 20. A distal end of the metal shaft 40 is in contact with a shaft portion 51 of the electrode member 50. The distal end portion of the metal shaft 40 is fixed to the shaft portion 51 of the electrode member 50 with an adhesive 60 while being in contact with the shaft portion 51. The proximal end portion of the metal shaft 40 is fitted over the base bottom protruding portion 23 of the base bottom member 20. The metal shaft 40 is compressed in the length direction by the base bottom member 20 that is fitted into the proximal end of the body member 30 toward the distal end side.

It is preferred that the metal shaft 40 have pliability that allows bending in a radial direction with respect to an axis extending in the length direction of the skin stimulation brush pin 10. It is more preferred that the metal shaft 40 be formed of a coil spring that urges the electrode member 50 toward the distal end side. It is preferred that the coil spring, which corresponds to the metal shaft 40, constantly urge the electrode member 50 toward the distal end side. However, even in a case in which the coil spring does not constantly urge the electrode member 50 toward the distal end side, the coil spring is only required to urge the electrode member 50 toward the distal end side when the electrode member 50 is thrust toward the proximal end side. It is preferred that the coil spring be held and compressed between the base bottom member 20 and the electrode member 50.

In one example described in this embodiment, the metal shaft 40 is formed of a coil spring. However, the metal shaft 40 is not limited to a coil spring. The metal shaft 40 may be formed in various shapes as long as the base bottom member 20 and the electrode member 50 can be coupled to each other to allow conduction of electricity through the electrode member 50. The metal shaft 40 can be formed, for example, in a columnar body, a wire body, or a tubular body.

The electrode member 50 is connected to the distal end-side opening of the body member 30 and has a distal end being exposed. The electrode member 50 is formed as a solid block body. The electrode member 50 includes the shaft portion 51 having an elongated shape, which extends from an intermediate portion to a proximal end of the electrode member 50. An electrode stopper portion 52 having a flange-like shape is formed on a peripheral surface of an intermediate portion of the shaft portion 51. The shaft portion 51 of the electrode member 50 is fitted into the distal-end opening portion 34 of the body member 30. The electrode stopper portion 52 is engaged with the level difference formed at a proximal end of the radially contracted portion 33 of the body member 30. A proximal end portion of the shaft portion 51 is in contact with the distal end of the metal shaft 40. A proximal end portion of the electrode member 50 is fixed to the distal end of the metal shaft 40 with the adhesive 60 while being in contact with the distal end of the metal shaft 40. The electrode member 50 is urged toward the distal end side by the metal shaft 40, which is a coil spring. The distal end of the electrode member 50 has a curved surface.

The electrode member 50 may have corrosion resistance. It is more preferred that the electrode member 50 be made of stainless steel. Besides stainless steel, a metal containing chromium or a conductor that has been subjected to an anti-corrosive process such as plating is preferred for the electrode member 50. Further, copper, aluminum, silver, gold, or gold can also be used for the electrode member 50.

Further, the electrode member 50 is connected to the distal-end opening portion 34, which is the opening of the body member 30 on the distal end side, without leaving a gap. The electrode member 50 is connected to the distal-end opening portion 34 of the body member 30 while being in close contact therewith.

The adhesive 60 is supplied into the tubular inner portion of the body member 30, which surrounds the shaft portion 51 of the electrode member 50. The adhesive 60 fixes the proximal end portion of the electrode member 50 and the distal end of the metal shaft 40 under a state in which the proximal end portion and the distal end are in contact with each other. Various adhesives 60 such as, for example, a room temperature vulcanizing (RTV) rubber can be used as the adhesive 60. Further, it is preferred that the adhesive 60 be an electroconductive adhesive.

Now, actions and effects of the skin stimulation brush 1 are described in accordance with a procedure of use in one example of the skin stimulation brush 1 according to this embodiment.

First, a user of the skin stimulation brush 1 turns on a power source (not shown) for the skin stimulation brush 1, which is provided to the housing 2.

When the skin stimulation brush 1 described in one example of this embodiment is turned on, a current flows through the electric circuit 6. Further, the base bottom members 20 are connected to the electric circuit 6 so as to allow conduction of electricity from the electric circuit 6. More specifically, the base bottom members 20 are inserted into the through holes 7 while the pins 21 are in contact with the through holes 7. Thus, the current, which flows through the electric circuit 6, causes conduction of electricity through the base bottom members 20. Next, the metal shafts 40 are in contact with the base bottom members 20 conducting electricity. As a result, the current flows from the base bottom members 20 to the metal shafts 40. Further, the metal shafts 40 are in contact with the electrode members 50. Thus, the current that has flowed through the metal shafts 40 flows to the electrode members 50. Thus, the current is caused to flow through the electrode members 50.

Further, in the skin stimulation brush 1 described in one example of this embodiment, when the electric circuit 6 is configured to be capable of applying a low-frequency current to the base bottom members 20, for example, when the electric circuit 6 includes a low-frequency current generator or a low-frequency modulator, a low-frequency current is applied to the base bottom members 20. Thus, the low-frequency current flows from the base bottom members 20 via the metal shafts 40 to the electrode members 50.

Next, a massage is given while the skin stimulation brush 1 including the electrode members 50 conducting electricity is held in contact with skin. In this case, the electrode members 50 having the distal ends exposed from the body members 30 are brought into contact with skin to apply electric stimulation and pressure stimulation to the skin.

As skin, skin all over the body, which includes a scalp, may be a target. For example, sebum, water, shampoo, or a cosmetic product may adhere to a scalp and skin all over the body, or body hair growing therefrom. These liquids may degrade a related-art skin stimulation brush to lower its electroconductivity. Specifically, some bristles used for related-art skin stimulation brushes are made of a metal or an electroconductive resin. When skin is to be stimulated with use of these bristles, the following problems may arise. When skin is stimulated with use of bristles made of a metal, there is a problem in that, for example, water adhering to skin may corrode a metal of the bristles to thereby lower electroconductivity. Further, when the bristles are made of an electroconductive resin, there is a problem in that the resin absorbs water or the like and degrades to thereby lower the electroconductivity of the electroconductive resin. These problems may reduce a lifetime of the skin stimulation brush itself. Thus, user's need to maintain intensity of electric stimulation over a long period of time cannot be sufficiently satisfied.

Thus, in the skin stimulation brush 1 described in one example of this embodiment, the metal shaft 40, which serves as a current path, is inserted into the tubular inner portion of the body member 30. Thus, the metal shaft 40 is not brought into direct contact with sebum, water, shampoo, a cosmetic product, or the like, which adheres to skin or body hair. As a result, corrosion of the metal shaft 40, which serves as a current path from the electric circuit 6 to the electrode member 50, can be suppressed, and thus lowering of electroconductivity can be suppressed for a long period of time. Further, this allows intensity of electric stimulation to skin to be maintained over a long period of time. Thus, a lifetime not only as the metal shaft 40 but also as the skin stimulation brush 1 as a whole can be extended.

Further, nonuniformity in degradation, that is, degradation in electroconductivity of only some of the plurality of skin stimulation brush pins 10 mounted to the skin stimulation brush 1 described in one example of this embodiment due to adhesion of, for example, a cosmetic product, can be prevented.

Further, when the body member 30 of the skin stimulation brush 1 described in one example of this embodiment has water resistance, the body member 30 into which the metal shaft 40 is inserted does not easily allow water to pass into the tubular inner portion. Thus, the metal shaft 40 is not brought into contact with liquid. Accordingly, a more remarkable effect of suppressing the corrosion of the metal shaft 40 is obtained.

When the body member 30 of the skin stimulation brush 1 described in one example of this embodiment is made of a silicone rubber, excellent water resistance can be obtained owing to physical properties of the silicone rubber to thereby prevent the corrosion of the metal shaft 40. Further, when the body member 30 is made of a silicone rubber, the body member 30 has elasticity that allows bending in the radial direction. Further, when the body member 30 is made of a silicone rubber, the body member 30 also has flexibility in the length direction.

When the electrode members 50 of the skin stimulation brush 1 described in one example of this embodiment has corrosion resistance, the corrosion of the electrode members 50 can be suppressed. Thus, lowering of electroconductivity of the electrode members 50 can be suppressed.

Further, when the electrode member 50 of the skin stimulation brush 1 described in one example of this embodiment is made of stainless steel, the electrode member 50 has corrosion resistance. Thus, the corrosion of the electrode member 50 can be suppressed to thereby suppress lowering of electroconductivity. In addition, when the electrode member 50 is made of stainless steel, the corrosion of the electrode member 50 can be suppressed over a longer period of time and lowering of electroconductivity can be suppressed owing to a characteristic that a passivation film is regenerated. The passivation film of stainless steel is extremely thin, and thus does not inhibit an electric stimulation effect on skin. Further, when the electrode member 50 is made of stainless steel, processibility and strength of the electrode member 50 can easily be improved.

Further, when the body member 30 and the electrode member 50 of the skin stimulation brush 1 described in one example of this embodiment are connected to each other without leaving a gap, intrusion of liquid or moisture through a gap between the body member 30 and the electrode member 50 into the inside of the tubular body of the body member 30 can be suppressed. As a result, the corrosion of the metal shaft 40 can be suppressed to thereby suppress lowering of electroconductivity.

Further, when the brush base 4 and the body member 30 of the skin stimulation brush 1 described in one example of this embodiment are connected to each other without leaving a gap, intrusion of liquid or moisture through a gap between the body member 30 and the brush base 4 into the inside of the tubular body of the body member 30 can be suppressed. As a result, the corrosion of the metal shaft 40 or the base bottom member 20 can be suppressed to thereby suppress lowering of electroconductivity.

When the body member 30 and the electrode member 50 are in close contact with each other at their connecting portion without leaving a gap and the body member 30 and the brush base 4 are in close contact with each other at their connecting portion without leaving a gap, liquid or moisture can be prevented from intruding into the body member 30. In particular, lowering of electroconductivity of the skin stimulation brush 1 can be prevented, and a lifetime of the skin stimulation brush 1 can be extended. Further, this configuration can easily be achieved by using the body member 30 having elasticity such as a silicone rubber.

When the distal end of the electrode member 50 of the skin stimulation brush 1 described in one example of this embodiment has a curved surface, contact of the electrode member 50 with skin can provide comfortable feeling.

Next, the skin stimulation brush pins 10 of the skin stimulation brush 1 are brought into contact with skin obliquely with respect to a skin surface.

In this case, when the metal shaft 40 of the skin stimulation brush 1 described in one example of this embodiment has pliability that allows bending in the radial direction and the body member 30 has elasticity that allows bending in the radial direction, the body member 30 and the metal shaft 40 can be integrally bent in the radial direction. As a result, skin is pressed with the restoring force generated due to the elasticity of the body members 30 to thereby provide an excellent massaging effect.

Further, when the metal shaft 40 of the skin stimulation brush 1 described in one example of this embodiment has a second elasticity, a second restoring force generated due to the second elasticity of the metal shaft 40 acts in addition to the restoring force generated due to the elasticity of the body member 30. As a result, the skin can be pressed more strongly. Thus, a further excellent massaging effect can be obtained while electric stimulation is applied to skin. Further, for example, when the metal shaft 40 is formed of a spring, the above-mentioned second elasticity can be obtained. An axially elongated spring is preferred as the spring. More specifically, suitable examples of the spring include a leaf spring and a coil spring. In particular, a coil spring is preferred because the coil spring enables easy mounting of the electrode member 50. More specifically, when the metal shaft 40 is a coil spring, the electrode member 50 and the metal shaft 40 can easily be connected by winding the coil spring around a shaft-shaped portion, specifically, the shaft portion 51 of the electrode member 50 inserted into the distal-end opening portion 34. Further, as illustrated in FIG. 4, it is preferred that the metal shaft 40 be inserted with an air gap 36 from an inner surface 35 of the body member 30. With the air gap 36, the metal shaft 40 can be bent without interfering with the body member 30 in a bending operation of the body member 30 in the radial direction.

Next, the skin stimulation brush pins 10 of the skin stimulation brush 1 are brought into contact with skin perpendicularly from above with respect to a skin surface.

In this case, when each of the metal shafts 40 of the skin stimulation brush 1 described in one example of this embodiment is formed of a coil spring, the electrode member 50 can be thrust toward the proximal end side against an urging force of the coil spring. Thus, when the electrode member 50 presses skin, an impact generated by the contact of the electrode member 50 with the skin can be alleviated. As a result, a degree of pressure exerted by the user on the skin stimulation brush 1 can easily be adjusted.

Further, the urging force of the coil spring is transmitted to the distal end side of the electrode member 50 under a state in which the electrode member 50 is thrust toward the proximal end side. As a result, the electrode member 50 can press the skin to thereby achieve a further excellent massage.

Further, the electrode member 50 is not limited to be thrust toward the proximal end side together with the body member 30. For example, the electrode member 50 may be thrust toward the proximal end side while sliding with respect to the distal-end opening portion 34 of the body member 30.

Further, when the body member 30 of the skin stimulation brush 1 described in one example of this embodiment has flexibility in the length direction and the body member 30 is compressed in the length direction when the electrode member 50 is thrust toward the proximal end side, not only the urging force of the coil spring but also the restoring force toward the distal end side of the body member 30 being in a compressed state acts on the electrode member 50. Thus, the contact between skin and the electrode members 50 can be more reliably achieved, and stronger pressure stimulation can be obtained. In the skin stimulation brush 1 described in this embodiment, when the body member 30 is compressed, the inner diameter of the tubular inner portion is increased. Thus, the degree of compression of the body member 30 can be increased. As a result, stronger pressure feeling can be obtained.

Other actions and effects of the skin stimulation brush 1 described in one example of this embodiment are described.

With the skin stimulation brush 1 described in one example of this embodiment, the low-frequency current applied from the electrode members 50 to skin can increase blood flow in the skin to activate the metabolism of cells. Thus, when the skin of an area having hair is stimulated, hair loss can be suppressed. Further, when a facial skin is stimulated, a rapid skin lift-up effect can be exerted. Thus, a skin condition before makeup is improved, and thus makeup sits better.

Further, the skin lift-up effect can also contribute to a firming effect on a skin other than a facial skin, and can suppress sagging of the skin.

The proximal end portion of the body member 30 of the skin stimulation brush 1 described in one example of this embodiment is fixed by the inner surface of the housing 2 and a surface of the electric circuit 6, which is opposed to the housing 2. Thus, problems such as removal of the skin stimulation brush pins 10 from the brush-base holes 5 or forcing the skin stimulation brush pins 10 deeply into the brush-base holes 5 can be suppressed.

Further, in the skin stimulation brush 1 described in one example of this embodiment, the electrode stopper portion 52 of the electrode member 50 is engaged with the radially contracted portion 33 of the body member 30. Thus, removal of the electrode member 50 from the distal-end opening portion 34 of the body member 30 can be suppressed.

Further, in the skin stimulation brush 1 described in one example of this embodiment, the coil spring is sandwiched and compressed between the base bottom member 20 and the electrode member 50. Thus, an extension force is accumulated in the coil spring, and the contact between the coil spring, and the base bottom member 20 and the electrode member 50 can be more reliably achieved.

Further, in the skin stimulation brush 1 described in one example of this embodiment, a contact portion between the metal shaft 40 and the electrode member 50 is fixed with the adhesive 60. Further, an RTV rubber, which can be bonded to a silicone rubber, can be used as the adhesive 60. Thus, the contact between the metal shaft 40 and the electrode member 50 can be further reliably achieved, and the removal of the electrode member 50 from the body member 30 made of a silicone rubber can be prevented.

Further, when an electroconductive adhesive is used as the adhesive 60 for the skin stimulation brush 1 described in one example of this embodiment, a current, which flows through the adhesive 60, can cause conduction of electricity through the electrode member 50 even if the metal shaft 40 and the electrode member 50 are separated from each other.

Further, with a configuration in which the base bottom protruding portion 23 of the skin stimulation brush 1 described in one example of this embodiment is fitted into the proximal end portion of the coil spring, positioning at the proximal end portion of the coil spring is reliably achieved. Thus, electrical connection between the base bottom member 20 and the coil spring is reliably achieved.

It should be noted that the above-mentioned actions and effects are actions and effects of the skin stimulation brush 1 described in one example of this embodiment. Thus, the technical scope of the present invention is not limited by the actions and effects of this embodiment.

REFERENCE SIGNS LIST 1 skin stimulation brush
2 housing
3 handle
4 brush base
5 brush-base hole
6 electric circuit
7 through hole
10 skin stimulation brush pin
20 base bottom member
21 pin
22 base bottom flange
23 base bottom protruding portion
30 body member
31 proximal-end opening portion
32 body stopper portion
33 radially contracted portion 34 distal-end opening portion
36 air gap
40 metal shaft
50 electrode member
51 shaft portion
52 electrode stopper portion
60 adhesive

The invention claimed is:

1. A skin stimulation brush, comprising:
   a housing that forms a handle and a brush base provided to one end of the handle;
   an electric circuit accommodated in the housing; and
   a plurality of skin stimulation brush pins provided to the brush base in a protruding manner,
   wherein each of the skin stimulation brush pins includes:
   a base bottom member made of a metal, which is connected to the electric circuit so as to allow conduction of electricity from the electric circuit;
   a body member being an elongated tubular body, which has a proximal end portion at which the base bottom member is disposed;
   an electrode member, which is connected to an opening of the body member on a distal end side, and has a distal end being exposed, wherein the electrode member includes a shaft portion having an elongated shape, which extends from an intermediate portion to a proximal end of the electrode member, and the shaft portion of the electrode member is fitted into the distal-end opening portion of the body member; and
   a metal shaft inserted into a tubular inner portion of the body member with an air gap, which is configured to couple the base bottom member and the electrode member while being in a compressed state in a length direction of the body member,
   wherein the metal shaft has pliability that allows bending in a radial direction, and
   wherein the body member has elasticity that allows bending in a radial direction.

2. The skin stimulation brush according to claim 1, wherein the metal shaft is a spring configured to urge the electrode member toward a distal end side.

3. The skin stimulation brush according to claim 1, wherein the metal shaft is a coil spring configured to urge the electrode member toward a distal end side.

4. The skin stimulation brush according to claim 1,
   wherein the body member has flexibility in the length direction, and
   wherein, when the electrode member is thrust toward a proximal end side, the body member is compressed in the length direction.

5. The skin stimulation brush according to claim 1, wherein the body member and the brush base are formed integrally.

6. The skin stimulation brush according to claim 1, wherein the base bottom member is formed integrally with a proximal end portion of the metal shaft as a part of the metal shaft.

7. The skin stimulation brush according to claim 1, wherein the electrode member has corrosion resistance.

8. The skin stimulation brush according to claim 1, wherein the electrode member is made of stainless steel.

9. The skin stimulation brush according to claim 1, wherein the body member has water resistance.

10. The skin stimulation brush according to claim 1, wherein the body member is made of a silicone rubber.

11. The skin stimulation brush according to claim 1, wherein the electric circuit is configured to be capable of applying a low-frequency current to the electrode member from the base bottom member via the metal shaft.

12. The skin stimulation brush according to claim 1, wherein the body member includes a radially contracted portion on the distal end side of the body member, the radially contracted portion radially protruding toward the electrode member.

* * * * *